US009795780B2

(12) United States Patent
Serna et al.

(10) Patent No.: US 9,795,780 B2
(45) Date of Patent: Oct. 24, 2017

(54) SYSTEM FOR DENERVATION

(71) Applicant: ABBOTT CARDIOVASCULAR SYSTEMS INC., Santa Clara, CA (US)

(72) Inventors: Benny Serna, Gilroy, CA (US);
Stephen Pacetti, San Jose, CA (US);
John Stankus, Campbell, CA (US)

(73) Assignee: Abbott Cardiovascular Systems Inc., Santa Clara, CA (US)

(*) Notice: Subject to any disclaimer, the term of this patent is extended or adjusted under 35 U.S.C. 154(b) by 188 days.

(21) Appl. No.: 14/574,684

(22) Filed: Dec. 18, 2014

(65) Prior Publication Data

US 2016/0175582 A1   Jun. 23, 2016

(51) Int. Cl.
| | |
|---|---|
| *A61N 1/05* | (2006.01) |
| *A61N 1/36* | (2006.01) |
| *A61N 7/00* | (2006.01) |
| *A61M 25/10* | (2013.01) |
| *A61B 18/08* | (2006.01) |
| *A61B 18/14* | (2006.01) |

(Continued)

(52) U.S. Cl.
CPC ............ *A61N 1/0551* (2013.01); *A61B 18/08* (2013.01); *A61B 18/1492* (2013.01); *A61M 25/1029* (2013.01); *A61M 25/10184* (2013.11); *A61N 1/36117* (2013.01); *A61N 7/00* (2013.01); *A61B 2018/0022* (2013.01); *A61B 2018/00214* (2013.01); *A61B 2018/00404* (2013.01); *A61B 2018/00434* (2013.01); *A61B 2018/00511* (2013.01); *A61B 2018/0212* (2013.01); *A61B 2018/0262* (2013.01); *A61B 2018/044* (2013.01); *A61B 2018/1435* (2013.01); *A61N 2007/003* (2013.01); *A61N 2007/0021* (2013.01); *A61N 2007/0026* (2013.01)

(58) Field of Classification Search
CPC ........ A61M 25/10184; A61M 25/1029; A61N 1/36117; A61N 2007/003; A61N 1/0551; A61N 2007/0021; A61N 2007/0026; A61N 7/00; A61B 18/08; A61B 18/1492; A61B 2018/00214; A61B 2018/0022; A61B 2018/00404; A61B 2018/00434; A61B 2018/00511; A61B 2018/0212; A61B 2018/0262; A61B 2018/044; A61B 2018/1435
See application file for complete search history.

(56) References Cited

U.S. PATENT DOCUMENTS 5,170,802 A   12/1992  Mehra
5,295,959 A *  3/1994  Gurbel ................ A61M 25/104
                                                              604/103

(Continued)

*Primary Examiner* — Ruth S Smith
(74) *Attorney, Agent, or Firm* — David J. Pitman; Fulwider Patton LLP

(57) ABSTRACT

An apparatus for vascular denervation, comprising a catheter configured for delivery into a vessel of a patient. A balloon is mounted on a distal tip of the catheter, the balloon being configured to be inflatable and further configured so that, upon inflation, the balloon adopts a shape that includes a first edge and a second edge that wind around each other in a double helix, the first edge and the second edge being separated from each other by a first crease and a second crease that also wind around each other in a double helix. A first electrode is attached to the balloon and is located to extend along the first edge.

6 Claims, 7 Drawing Sheets

(51) Int. Cl.
  *A61B 18/00*  (2006.01)
  *A61B 18/02*  (2006.01)
  *A61B 18/04*  (2006.01)

(56) References Cited

U.S. PATENT DOCUMENTS

| | | | |
|---|---|---|---|
| 5,383,856 A * | 1/1995 | Bersin | A61M 25/104 604/101.01 |
| 5,840,031 A * | 11/1998 | Crowley | A61B 8/12 600/440 |
| 7,937,143 B2 | 5/2011 | Demarais et al. | |
| 2011/0160575 A1 * | 6/2011 | Beyar | A61M 25/104 600/424 |
| 2011/0257562 A1 * | 10/2011 | Schaer | A61N 7/022 601/2 |
| 2011/0264086 A1 | 10/2011 | Ingle | |
| 2012/0029509 A1 | 2/2012 | Smith | |
| 2012/0310233 A1 * | 12/2012 | Dimmer | A61B 18/1492 606/33 |
| 2014/0243807 A1 * | 8/2014 | Margolis | A61B 18/1492 606/20 |
| 2016/0256216 A1 * | 9/2016 | Chang | A61B 18/1492 |

\* cited by examiner

SYSTEM FOR DENERVATION

BACKGROUND

This invention relates to methods and devices for treatment of diseases that include congestive heart failure, chronic renal failure and hypertension. Specifically, the invention relates to improving conditions in patients by modulating or blocking signals to the renal nerve.

Congestive Heart Failure (CHF) is a form of heart disease that is becoming ever more common. The number of patients with CHF is expected to grow in increasing numbers as the so-called "Baby Boomers" reach 50 years of age. CHF is a health condition that occurs when the heart becomes damaged, resulting in a reduced blood flow to the organs of the body. If blood flow decreases sufficiently, kidney function becomes impaired and results in fluid retention, abnormal hormone secretions and increased constriction of blood vessels. These results increase the stress on the heart to do work, and further decrease the capacity of the heart to pump blood through the kidney and vascular circulation system. This reduced capacity further reduces blood flow to the kidney. It is believed that this cycle of reduced kidney perfusion is the principal non-cardiac cause perpetuating a patient's downward spiral into CHF. Moreover, the fluid overload and associated clinical symptoms resulting from these changes are predominant causes for excessive hospital admissions, reduced quality of life and overwhelming costs to the health care system.

While many different diseases may cause initial damage to the heart, once such damage is present, CHF is identifiable under two types: Chronic CHF and Acute CHF. Despite its name, the chronic form is the less acute form of the two but is a longer term, slowly progressive, degenerative disease and may lead to cardiac insufficiency. Chronic CHF is clinically categorized by the patient's mere inability to exercise or perform normal activities of daily living.

By contrast, patients with Acute CHF may experience a more severe deterioration in heart function than those with Chronic CHF. The Acute form results in the inability of the heart to maintain sufficient blood flow and pressure to keep vital organs of the body alive. This condition can occur when extra stress (such as by infection) significantly increases the workload on the heart in a patient with an otherwise stable form of CHF. By contrast to a mere stepwise downward progression that is observable in patients with Chronic CHF, a patient suffering Acute CHF may deteriorate rapidly from even the earliest stages of CHF to severe hemodynamic collapse. Moreover, Acute CHF can occur within hours or days following an Acute Myocardial Infarction (AMI), which is a sudden, irreversible injury to the heart muscle, identified in common parlance as a heart attack.

Against this background, the kidneys are known to play an important regulatory role in maintaining the homeostatic balance of the body. The kidneys eliminate foreign chemicals from the body, regulate inorganic substances, and function as endocrine glands to secrete hormonal substances like renin and erythropoietin. The main functions of the kidney are to maintain the water balance of the body and control metabolic homeostasis by making the urine more or less concentrated, thus either reabsorbing or excreting more fluid. However, when renal disease arises, some otherwise ordinary and regular physiological functions may become detrimental to the patient's health. When this occurs, the process is known as overcompensation. In the case of Chronic Renal Failure (CRF) the event of overcompensation may manifest itself as hypertension that has the effect of damaging the heart and blood vessels, and can eventually result in a stroke or death. Thus, without proper function by the kidneys, a patient may suffer water retention, reduced urine flow, and an accumulation of waste toxins in the blood and body. These conditions resulting from reduced renal function, or renal failure (kidney failure), tend to increase the workload placed upon the heart. In a patient, simultaneous occurrence of both CRF and CHF may cause the heart to further deteriorate as the water build-up and blood toxins accumulate due to the poorly functioning kidneys and may, in turn, cause the heart further harm.

It has been observed, in connection with human kidney transplantation, that there is evidence to suggest that the nervous system plays a major role in kidney function. It was noted for example that after a transplant, when all the renal nerves are severed, the kidney was observed to increase excretion of water and sodium. This phenomenon has also been observed in animals when renal nerves are cut or chemically destroyed. The phenomenon has been termed "denervation diuresis" because the denervation acted on a kidney in a similar way to a diuretic medication. Later, observation of "denervation diuresis" was found to be associated with vasodilatation of the renal arterial system that led to the increase of the blood flow through the kidney. This observation was confirmed by the further observation in animals that reducing blood pressure supplying the kidney could reverse the "denervation diuresis".

It was also observed that after several months passed after kidney transplant surgery in successful cases, the "denervation diuresis" in transplant recipients stopped, and the kidney function returned to normal. Initially, it was believed that "renal diuresis" is merely a passing phenomenon and that the nerves conducting signals from the central nervous system to the kidney are not essential for kidney function. Later discoveries led to the present generally held conclusion that the renal nerves have an ability to regenerate, and that the reversal of the "denervation diuresis" is attributable to the growth of the new nerve fibers supplying kidneys with the necessary stimuli.

In summary then, it is known from clinical experience and also from the existing large body of animal research that stimulation of the renal nerve leads to the vasoconstriction of blood vessels supplying the kidney, decreased renal blood flow, decreased removal of water and sodium from the body and increased renin secretion. It is also known that reduction of the sympathetic renal nerve activity, achieved by renal denervation, can beneficially reverse these processes.

There has therefore already been identified a need in the art for methods and devices that may apply the observed effects set forth above to halt and reverse the symptoms of Congestive Heart Failure. Thus, certain methods and devices have already been developed in the art to reduce renal nerve activity, in order to meet the aforesaid need. For example, the following patents and applications are directed to the stated need: U.S. Pat. No. 8,347,891, and U.S. Application 2012/0143293. In some approaches configured to induce selective damage to the renal nerves (renal denervation), manufacturers have developed and used radio frequency (RF) catheters, which, while being minimally invasive, have problems related to positioning electrodes within a vessel, and maintaining uniform contact between the electrodes and the vessel wall. For example, in certain systems for denervation, treatment assemblies are used which comprise balloon structure for supporting a plurality of electrodes which are deployed to place the electrodes in contact with a vessel wall. Experience of using these systems reveals that problems arise in use because the balloon tends to block the flow of blood in the vessel for possibly extended periods of time, with adverse effects for the patient.

Thus, there is a need in the medical arts to produce a system and method for RF-based renal therapy which is relatively simple, accurate, effective, and produces an enhanced measure of electrode apposition control, and also permits blood flow during use. The present invention addresses these and other needs

SUMMARY OF THE INVENTION

In some embodiments, the invention is an apparatus for vascular denervation, comprising a catheter configured for delivery into a vessel of a patient. A balloon is mounted on a distal tip of the catheter, the balloon being configured to be inflatable and further configured so that, upon inflation, the balloon adopts a shape that includes a first edge and a second edge that wind around each other in a double helix, the first edge and the second edge being separated from each other by a first crease and a second crease that also wind around each other in a double helix. A first means for delivering energy is attached to the balloon and located to extend along the first edge. In some embodiments, the apparatus further includes a second means for delivering energy attached to the balloon and located to extend along the second edge. In some embodiments, the first means for delivering energy is an electrode, and in other embodiments, the first means for delivering energy is an ultrasound transducer. In some embodiments, the balloon is configured to define a plurality of micro-pores sized to permit inflation fluid to leak out of the balloon. In some embodiments, the balloon is formed from opposing surfaces of polymer material, wherein the opposing surfaces are joined to each other at intermittent locations such that some portions of the opposing surfaces are connected and other portions of the opposing surfaces are not connected.

In another aspect, the invention is a method for manufacturing a vascular denervation device. The method comprises providing a length of polymer material having a cylindrical form in an inflated condition about a central axis. The polymer material is configured to have a flattened shape in a deflated condition, wherein opposing surfaces of the polymer material are in contact with each other. The opposing surfaces are bonded to each other along at least two lines that define a space between the two lines, the space including the central axis. At least one means for delivering energy is attached to an edge of the polymer material that extends parallel to the central axis. A catheter portion is inserted into the space such that the catheter portion is coaxial with the central axis. The polymer material is twisted about the catheter portion, after which the polymer material is bonded in a twisted condition to the catheter portion. In some embodiments, the step of bonding the opposing surfaces to each other along at least two lines includes bonding the opposing surfaces to each other along at least four lines. In other embodiments, the method includes bonding the opposing surfaces to each other along opposite ends of the polymer material that extend perpendicular to the catheter portion. And in further embodiments, the method further includes bonding the opposing surfaces to each other along at least one line located between the opposite ends and extending perpendicular to the catheter portion. In yet further embodiments, the method further includes bonding the opposing surfaces to each other at a plurality of point locations.

In another aspect of the invention, the invention is a method for treating a patient. The method comprises inserting into a vessel of the patient a catheter that includes a balloon having an entire length mounted on a distal tip of the catheter, the balloon being configured to be inflatable and further configured so that, upon inflation, the balloon adopts a shape that includes a first edge and a second edge that wind around each other in a double helix, the first edge and the second edge being separated by a first crease and a second crease that also wind around each other in a double helix, and a first means for delivering energy fixed to the balloon and located to extend along the first edge thereby adopting a helical configuration. The method further includes inflating the balloon and, causing the first edge to urge the first means for delivering energy onto the vessel wall. Blood in the vessel is allowed to flow past the entire length of the balloon by passing through both the first crease and the second crease. Additionally energy is delivered to the means for delivering energy. In some embodiments, the method of delivering energy includes delivering electric energy, and in other embodiments, it includes delivering ultrasonic energy. In further embodiments, delivering energy is carried out simultaneously with allowing blood in the vessel to flow past the entire length of the inflated balloon. This simultaneous action allows the blood to cool the vessel wall surface at the same time as energy is being delivered into the tissue located deeper within the interstitial tissue of the vessel.

These and other advantages will become clearer when read in conjunction with the drawings and the detailed description of preferred embodiments.

BRIEF DESCRIPTION OF THE DRAWINGS

Many aspects of the present disclosure can be better understood with reference to the following drawings. The components in the drawings are not necessarily to scale. Instead, emphasis is placed on illustrating the principles of the present disclosure.

DETAILED DESCRIPTION OF THE PREFERRED EMBODIMENTS

Figure 1:
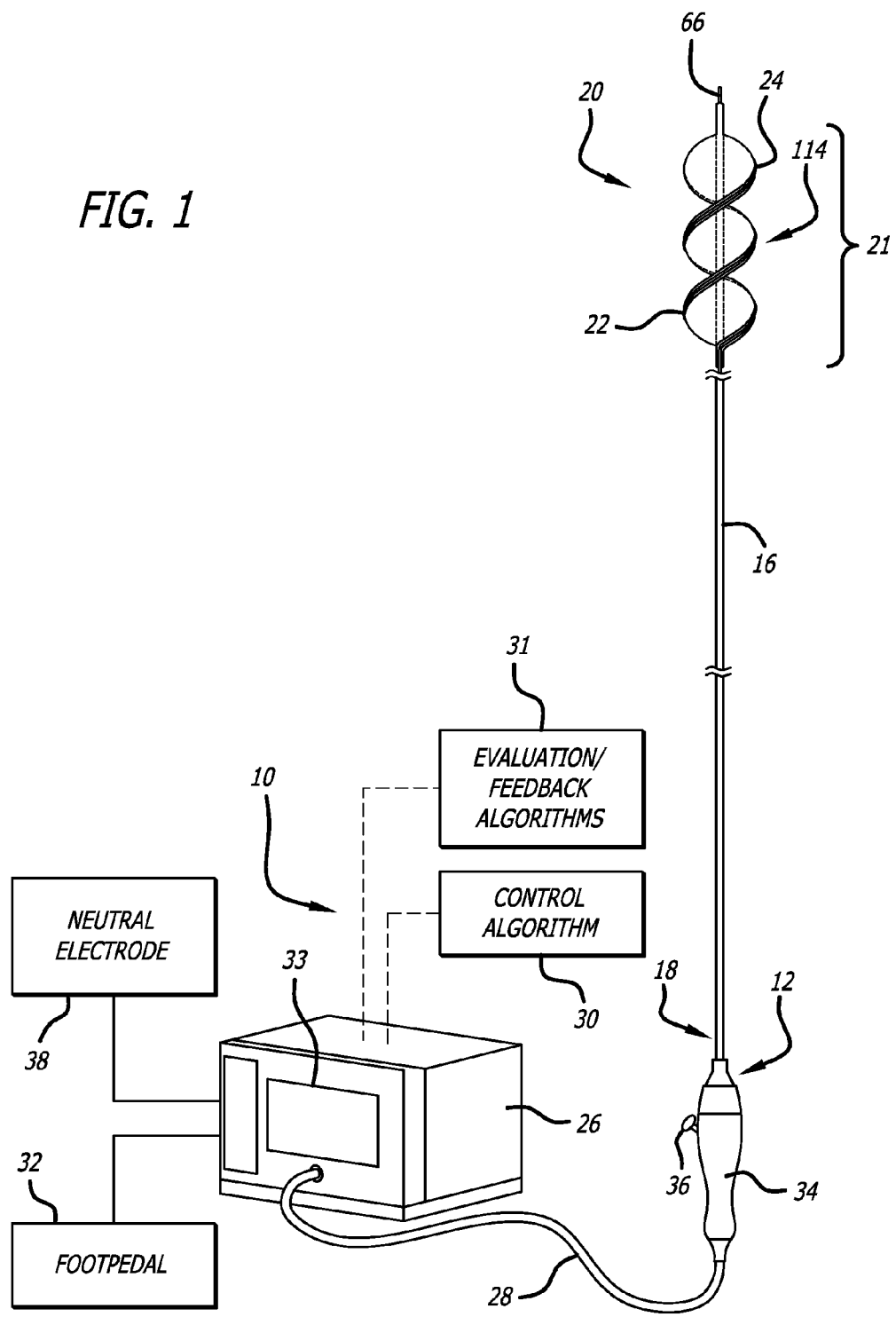
FIG. 1 illustrates an intravascular renal neuromodulation system configured in accordance with an embodiment of the present technology.

The applicants base the present application on the known discovery, as set forth above, that it may be desirable to perform a denervation treatment of the renal artery (renal denervation, or, renal neuromodulation) to positively affect a medical condition. In embodiments of the invention, such treatment may apply energy to zones of the renal artery normal to the artery wall. In some treatments, energy may be applied circumferentially. However, continuous circumferential lesions that extend continuously about a full 360° of the circumference of a cross-section normal to the body lumen or tissue in proximity to the body lumen may increase a risk of acute and/or late stenosis formation within the blood vessel. Therefore, embodiments described herein are directed to forming discrete lesions that do not form a circle in a single plane normal to the axis of the vessel.

Embodiments herein are configured to provide a non-continuous circumferential treatment that is performed over a lengthwise segment of the blood vessel (body lumen), as compared to a continuous circumferential treatment at a single normal cross-section or radial plane. Target structures such as nerves, including nerve fiber bundles, extending along the longitudinal dimension of the vessel are thus circumferentially affected, but not in continuous circumference about a single point of the vessel. Thus, the resulting lesion does not form a continuous circumferential lesion along any normal cross-section or radial plane of the vessel, but rather forms a helical lesion that may in some embodiments be a continuous helical lesion or in other embodiments a helical lesion with discontinuities along its path. This helical characteristic is believed to reduce the risk of acute or late stenosis formation within the blood vessel (body lumen) when compared with lesions that are formed to extend around a normal cross section of the vessel in single plane.

The non-continuous circumferential treatment is achieved in embodiments of the invention via apparatus positioned within a body lumen in proximity to target neural fibers for application of energy to the target neural fibers. The treatment may be induced, for example, via the application of electrical and/or electro-magnetic energy. Such treatment may be achieved, for example, via a thermal or non-thermal electric field, via a continuous or pulsed electric field, or via a stimulation electric field. Alternatively, the same effect may be achieved by using ultrasonic energy as a means for delivering energy, under which the same principles of the invention will be applicable.

In some embodiments, methods and apparatus for real-time monitoring of the treatment and its effects on the target or support structures, and/or in non-target tissue, may be provided. Likewise, real-time monitoring of the energy delivery apparatus may be provided. Power or total energy delivered, impedance and/or the temperature, or other characteristics of the target or non-target tissue, or of the apparatus, additionally or alternatively may be monitored.

When utilizing an electric field to achieve desired circumferentially non-continuous treatment, the electric field parameters may be altered and combined in any combination, as desired. Such parameters can include, but are not limited to, frequency, voltage, power, field strength, pulse width, pulse duration, the shape of the pulse, the number of pulses and/or the interval between pulses (e.g., duty cycle).

When utilizing thermal or indirect thermal mechanisms to achieve the desired treatment, protective elements may be provided to protect the non-target tissue (such as the smooth muscle cells) from thermal damage during the thermally-induced non-continuous circumferential treatment. For example, when heating target nerves or support structures located about a vessel, protective cooling elements, such as convective cooling elements, may be provided to protect the non-target tissue. Likewise, when cooling target nerves or support structures, protective heating elements, such as convective heating elements, may be utilized to protect the non-target tissue. Thermal energy may be applied either directly or indirectly for a brief or a sustained period of time in order to achieve, for example, desired neuromodulation or denervation. Feedback, such as sensed temperature and/or impedance, along target or non-target tissue or along the apparatus, may be used to control and monitor delivery of the thermal energy.

The non-target tissue optionally may be protected during, e.g., the neuromodulation or denervation, by utilizing blood flow as a conductive and/or convective thermal sink that absorbs excess thermal energy (hot or cold). For example, when blood flow is not blocked, the circulating blood may provide a relatively constant temperature medium for removing the excess thermal energy from the non-target tissue during the procedure. The non-target tissue additionally or alternatively may be protected by focusing the thermal (or other) energy on the target or support structures, such that an intensity of the energy is insufficient to induce thermal damage in the non-target tissue distant from the target or support structures.

Embodiments of Catheter Apparatus

FIG. 1 illustrates a renal neuromodulation system 10 configured in accordance with an embodiment of the present technology. The system 10 includes an intravascular intraluminal device 12 operably coupled to an energy source or energy generator 26. In the embodiment shown in FIG. 1, the intraluminal device 12 (e.g., a catheter) includes an elongated shaft 16 having a proximal portion 18, a handle 34 at a proximal region of the proximal portion 18, and a distal portion 20 extending distally relative to the proximal portion 18. The intraluminal device 12 further includes a treatment assembly or treatment section 21 (shown schematically, not to consistent scale) at the distal portion 20 of the shaft 16. As explained in further detail below, the treatment assembly 21 can include an array of two or more electrodes 24 configured to be delivered to a renal blood vessel (e.g., a renal artery) in a low-profile configuration. Upon delivery to the target treatment site within the renal blood vessel, the treatment assembly 21 is further configured to be deployed into an expanded state (e.g., a generally helical or spiral configuration) for delivering energy at the treatment site and providing therapeutically-effective electrically- and/or thermally-induced renal neuromodulation. In some embodiments, the treatment assembly 21 may be placed or transformed into the deployed state or arrangement via remote actuation, e.g., via an actuator 36, such as a knob, pin, or lever carried by the handle 34. In other embodiments, however, the treatment assembly 21 may be transformed between the delivery and deployed states using other suitable mechanisms or techniques.

The proximal end of the treatment assembly 21 is carried by or affixed to the distal portion of the elongated shaft 16. A distal end of the treatment assembly 21 may terminate the intraluminal device 12 with, for example, an atraumatic rounded tip or cap. Alternatively, the distal end of the treatment assembly 21 may be configured to engage another element of the system 10 or intraluminal device 12. For example, the distal end of the treatment assembly 21 may define a passageway for engaging a guide wire 66 for delivery of the intraluminal device using over-the-wire ("OTW") or rapid exchange ("RX") techniques.

The energy source or energy generator 26 (e.g., a RF energy generator) is configured to generate a selected form and magnitude of energy for delivery to the target treatment site via the electrodes 24. The energy generator 26 can be electrically coupled to the intraluminal device 12 via a cable 28. At least one supply wire (not shown) passes along the elongated shaft 16 or through a lumen in the elongated shaft 16 to the electrodes 24 and transmits the treatment energy to the electrodes 24. In some embodiments, each electrode 24 includes its own supply wire. In other embodiments, however, two or more electrodes 24 may be electrically coupled to the same supply wire. A control mechanism, such as a foot pedal 32 schematically identified in FIG. 1, may be connected (e.g., pneumatically connected or electrically connected) to the energy generator 26 to allow the operator to initiate, terminate and, optionally, adjust various operational characteristics of the generator, including, but not limited to, power delivery. The system 10 may also include a remote control device (not shown) that can be positioned in a sterile field and operably coupled to the electrodes 24. The remote control device is configured to allow for selectively turning on/off the electrodes. In other embodiments, the remote control device may be built into the handle assembly 34. The energy generator 26 can be configured to deliver the treatment energy via an automated control algorithm and/or under the control of the clinician. In addition, the energy generator 26 may include one or more evaluation or feedback algorithms to provide feedback to the clinician before, during, and/or after therapy.

Figure 2:
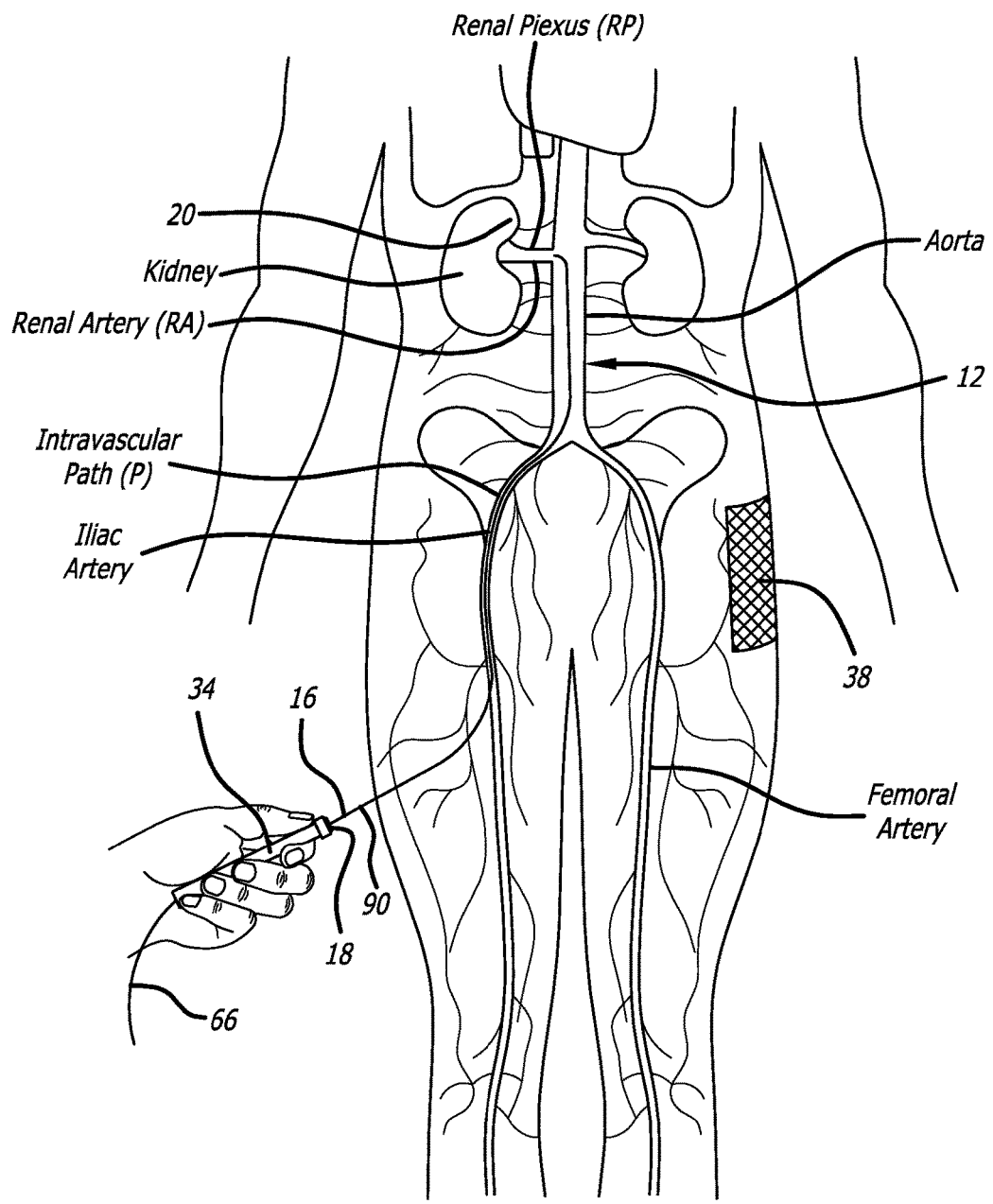
FIG. 2 illustrates modulating renal nerves with a multi-electrode catheter apparatus in accordance with an embodiment of the present technology.

In some embodiments, the system 10 may be configured to provide delivery of a monopolar electric field via the electrodes 24. In such embodiments, a neutral or dispersive electrode may be electrically connected to the energy generator 26 and attached to the exterior of the patient (as shown in FIG. 2). Additionally, one or more sensors (not shown), such as one or more temperature (e.g., thermocouple, thermistor, etc.), impedance, pressure, optical, flow, chemical or other sensors, may be located proximate to or within the electrodes 24 and connected to one or more supply wires (not shown). For example, a total of two supply wires may be included, in which both wires could transmit the signal from the sensor and one wire could serve dual purpose and also convey the energy to the electrodes 24. Alternatively, a different number of supply wires may be used to transmit energy to the electrodes 24.

The energy generator 26 may be part of a device or monitor that may include processing circuitry, such as a microprocessor, and a display. The processing circuitry may be configured to execute stored instructions relating to a control algorithm. The monitor may be configured to communicate with the intraluminal device 12 (e.g., via cable 28) to control power to the electrodes 24 and/or to obtain signals from the electrodes 24 or any associated sensors. The monitor may be configured to provide indications of power levels or sensor data, such as audio, visual or other indications, or may be configured to communicate the information to another device. For example, the energy generator 26 may also be configured to be operably coupled to a catheter lab screen or system for displaying treatment information.

FIG. 2 illustrates modulating renal nerves with an embodiment of the system 10. The intraluminal device 12 provides access to the renal plexus RP through an intravascular path P, such as a percutaneous access site in the femoral (illustrated), brachial, radial, or axillary artery to a targeted treatment site within a respective renal artery RA. As illustrated, a section of the proximal portion 18 of the shaft 16 is exposed externally of the patient. By manipulating the proximal portion 18 of the shaft 16 from outside the intravascular path P, the clinician may advance the shaft 16 through the sometimes tortuous intravascular path P and remotely manipulate the distal portion 20 of the shaft 16.

Image guidance, e.g., computed tomography (CT), fluoroscopy, intravascular ultrasound (IVUS), optical coherence tomography (OCT), or another suitable guidance modality, or combinations thereof, may be used to aid the clinician's manipulation. Further, in some embodiments, image guidance components (e.g., IVUS, OCT) may be incorporated into the intraluminal device 12 itself. After the treatment assembly 21 is adequately positioned in the renal artery RA, it can be radially expanded using the handle 34 or other suitable means until the electrodes 24 are in stable contact with the inner wall of the renal artery RA. The purposeful application of energy from the electrodes 24 is then applied to tissue to induce one or more desired neuromodulating effects on localized regions of the renal artery and adjacent regions of the renal plexus RP, which lay intimately within, adjacent to, or in close proximity to the adventitia of the renal artery RA. The purposeful application of the energy may achieve neuromodulation along all or at least a portion of the renal plexus RP.

The neuromodulating effects are generally a function of, at least in part, power, time, contact between the electrodes 24 and the vessel wall, and blood flow through the vessel. The neuromodulating effects may include denervation, thermal ablation, and non-ablative thermal alteration or damage (e.g., via sustained heating and/or resistive heating).

Figure 3A:
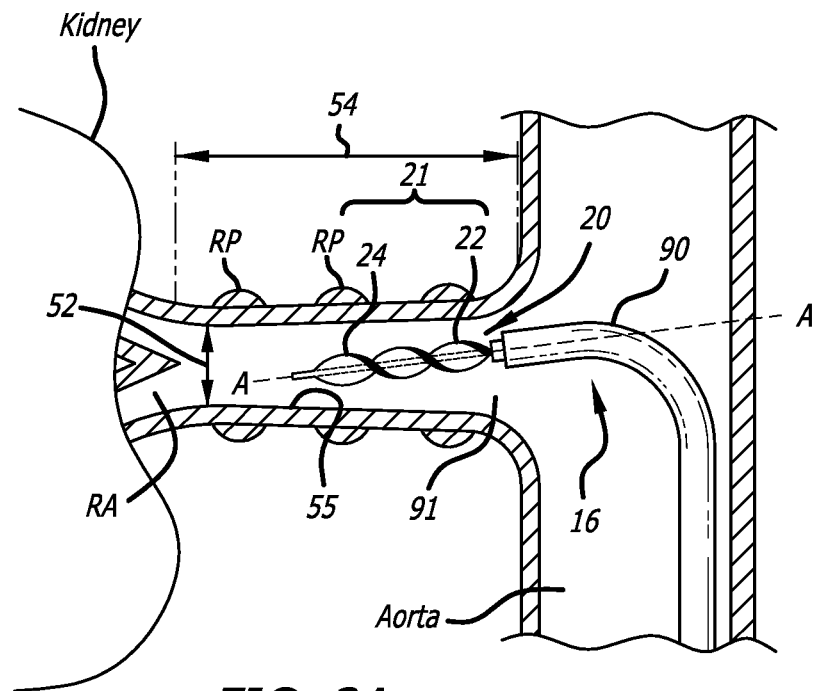
FIG. 3A is a view of a distal portion of a catheter shaft and a multi-electrode array in a delivery state (e.g., low-profile or collapsed configuration) within a renal artery used in conjunction with a guide catheter in accordance with an embodiment of the present technology.
Figure 3B:
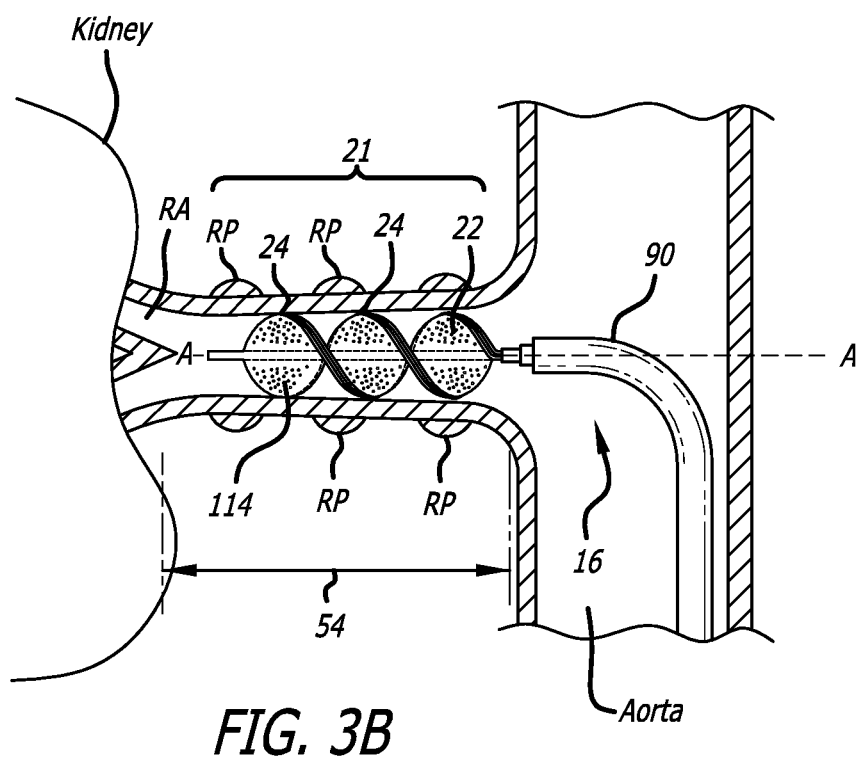
FIG. 3B is a view of the distal portion of the catheter shaft and the multi-electrode array of FIG. 3A in a deployed state (e.g., expanded configuration) within a renal artery in accordance with an embodiment of the technology.

Turning now to a more detailed description of certain embodiments, FIG. 3A is a schematic side view illustrating one embodiment of the distal portion of the shaft 16 and the treatment assembly 21 in a delivery state (e.g., low-profile or collapsed configuration) within a renal artery RA, and FIG. 3B illustrates the treatment assembly 21 in a deployed state (e.g., expanded or helical configuration) within the renal artery. Referring first to FIG. 3A, the collapsed or delivery arrangement of the treatment assembly 21 defines a low profile about the longitudinal axis A-A of the assembly such that a transverse dimension of the treatment assembly 21 is sufficiently small to define a clearance distance between an arterial wall 55 and the intraluminal device 12. The delivery state facilitates insertion and/or removal of the intraluminal device 12 and, if desired, repositioning of the treatment assembly 21 within the renal artery RA.

The distal portion 20 of the shaft 16 may flex in a substantial fashion to gain entrance into a respective left/right renal artery by following a path defined by a guide catheter, a guide wire, or a sheath. For example, the flexing of distal portion 20 may be imparted by the guide catheter 90, such as a renal guide catheter with a preformed bend near the distal end that directs the shaft 16 along a desired path, from the percutaneous insertion site to the renal artery RA. In another embodiment, the intraluminal device 12 may be directed to the treatment site within the renal artery RA by engaging and tracking a guide wire (e.g., guide wire 66 of FIG. 2) that is inserted into the renal artery RA and extends to the percutaneous access site. In operation, the guide wire is preferably first delivered into the renal artery RA and the elongated shaft 16 comprising a guide wire lumen is then passed over the guide wire into the renal artery RA.

After locating the treatment assembly 21 at the distal portion 20 of the shaft 16 in the renal artery RA, the treatment assembly 21 is transformed from its delivery state to its deployed state or deployed arrangement. The transformation may be initiated using an arrangement of device components as described herein with respect to the particular embodiments and their various modes of deployment. As described in greater detail below and in accordance with one or more embodiments of the present technology, the treatment assembly may be deployed by a deployment element, such as for example fluid pressure injected into the shaping structure of the treatment assembly to apply a deforming or shaping force to the assembly to transform it into its deployed state.

Further manipulation of the treatment assembly 21 and the electrodes 24 within the respective renal artery RA establishes apposition of the electrodes 24 against the tissue along an interior wall of the respective renal artery RA. For example, as shown in FIG. 3B, the treatment assembly 21 is expanded within the renal artery RA such that the electrodes 24 are in contact with the renal artery wall 55.

As best seen in FIG. 3B, in the deployed state, the treatment assembly 21 defines a substantially helical shaping structure 22 in contact with the renal artery wall 55 along a helical path. One advantage of this arrangement is that pressure from the shaping structure can be applied to a large range of radial directions without applying pressure to a circumference of the vessel. Thus, the helically-shaped treatment assembly 21 is configured to provide stable contact between the electrodes 24 and the artery wall 55 should the wall move in any direction under force supplied by the patient's anatomy. Furthermore, pressure applied to the vessel wall 55 along a helical path is less likely to stretch or distend a circumference of a vessel that lies in a single plane, and that could thereby cause injury to the vessel tissue. Still another feature of the expanded shaping structure is that it may contact the vessel wall in a large range of radially directed points and maintain a sufficiently open lumen in the vessel allowing blood to flow through the helix during therapy.

As best seen in FIG. 3B, in the deployed state, the shaping structure 22 defines a maximum axial length of the treatment assembly 21 that is approximately equal to or less than a renal artery length 54 of a main renal artery (i.e., a section of a renal artery proximal to a bifurcation). Because this length can vary from patient to patient, it is envisioned that the deployed helical-shaped shaping structure 22 may be fabricated in different sizes (e.g., with varying lengths and/or diameters) that may be appropriate for different patients. Referring to FIG. 3B, in the deployed state, the helical-shaped treatment assembly 21 provides for contact between the electrodes 24 and the inner wall 55 of the renal artery RA, where the points of contact do not lie in a single plane.

Turning now to an embodiment of a treatment assembly in the form of treatment apparatus as described in conjunction with the drawings in particular FIGS. 4-7, this embodiment includes a catheter based system for denervation in a patient. The system includes an elongate catheter 12 configured for insertion into the vasculature of a patient. Mounted on the distal tip of the catheter is a shaping structure 22 comprising an inflatable balloon 114 of novel and advantageous configuration, adapted to be inflated by known means such as delivery of saline or other suitable inflation fluid under pressure. To this end, the catheter defines an inflation lumen (not shown) of known configuration for transmission of the inflation fluid from the proximal end to the distally positioned balloon 114. It is known how to generally fabricate catheters, inflation lumens therein, and other internal lumens therein, and how to fabricate and attach cylindrical balloon for inflation on the end of a catheter. Teachings may be found, for example, in U.S. Pat. No. 7,951,259 which is incorporated herein by reference.

Figure 4:
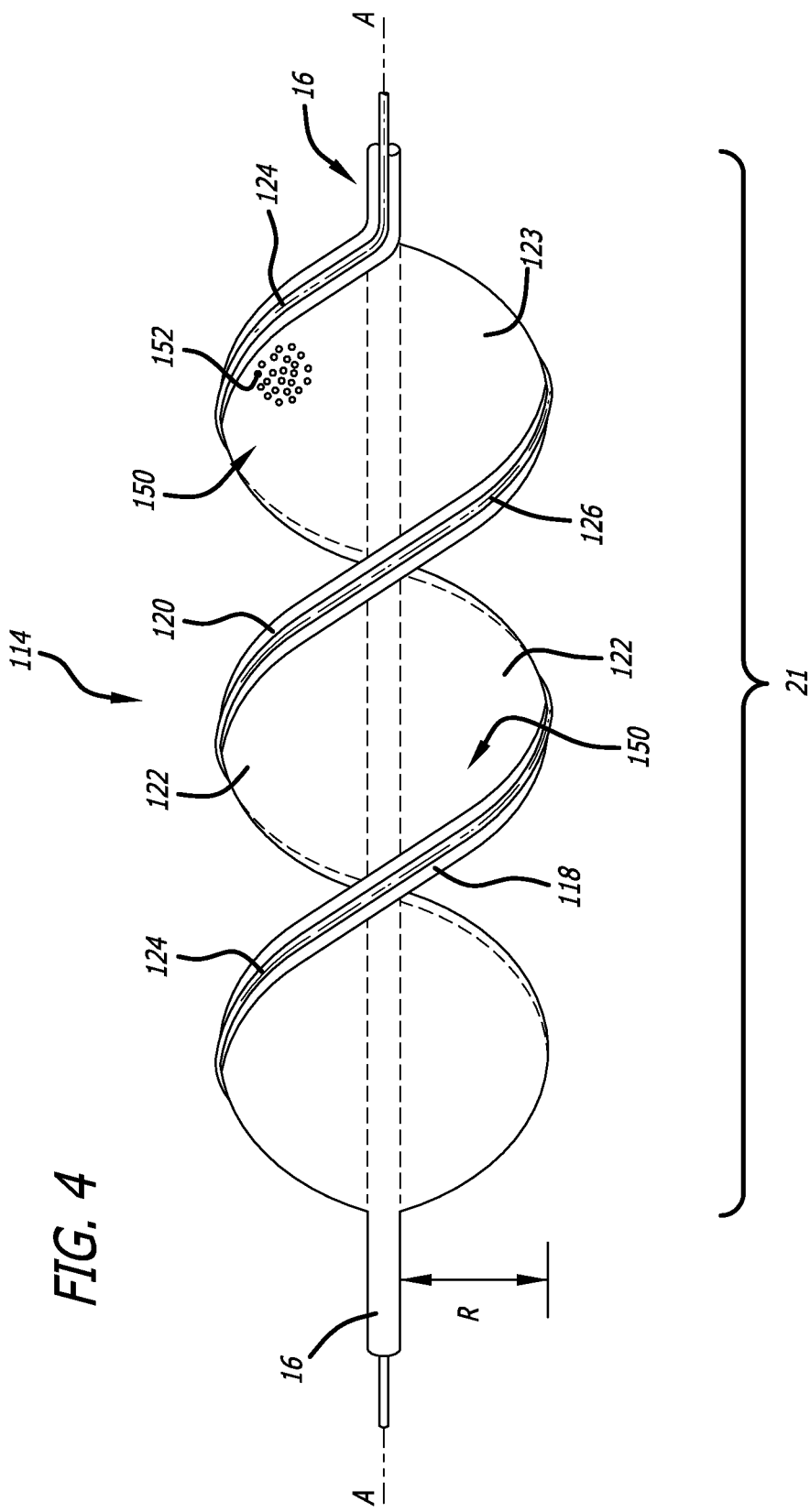
FIG. 4 is a schematic side view of a treatment system having components of the invention.
Figure 5:
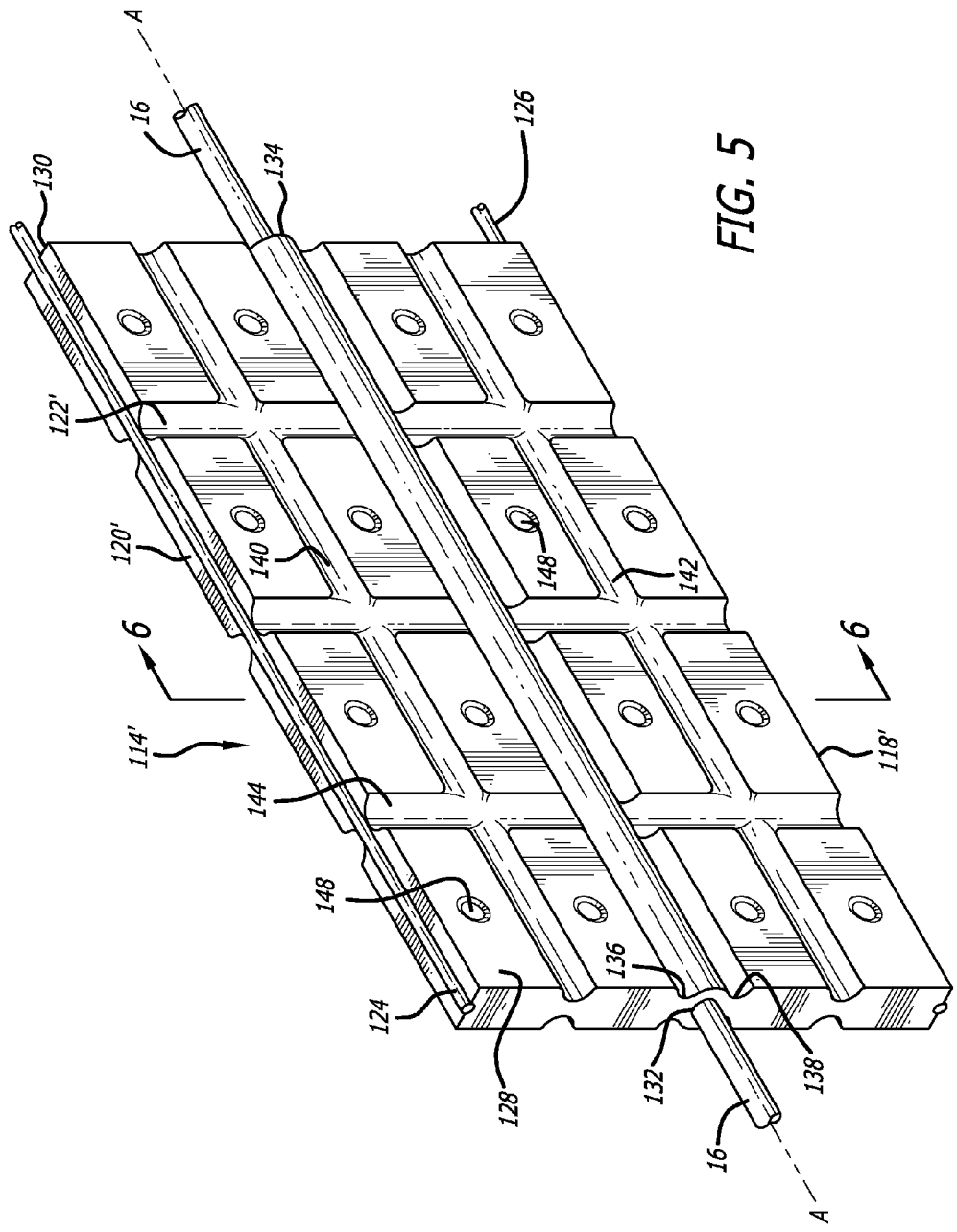
FIG. 5 is a perspective schematic view of a balloon structure having features of the invention, in a process of assembly.
Figure 6:
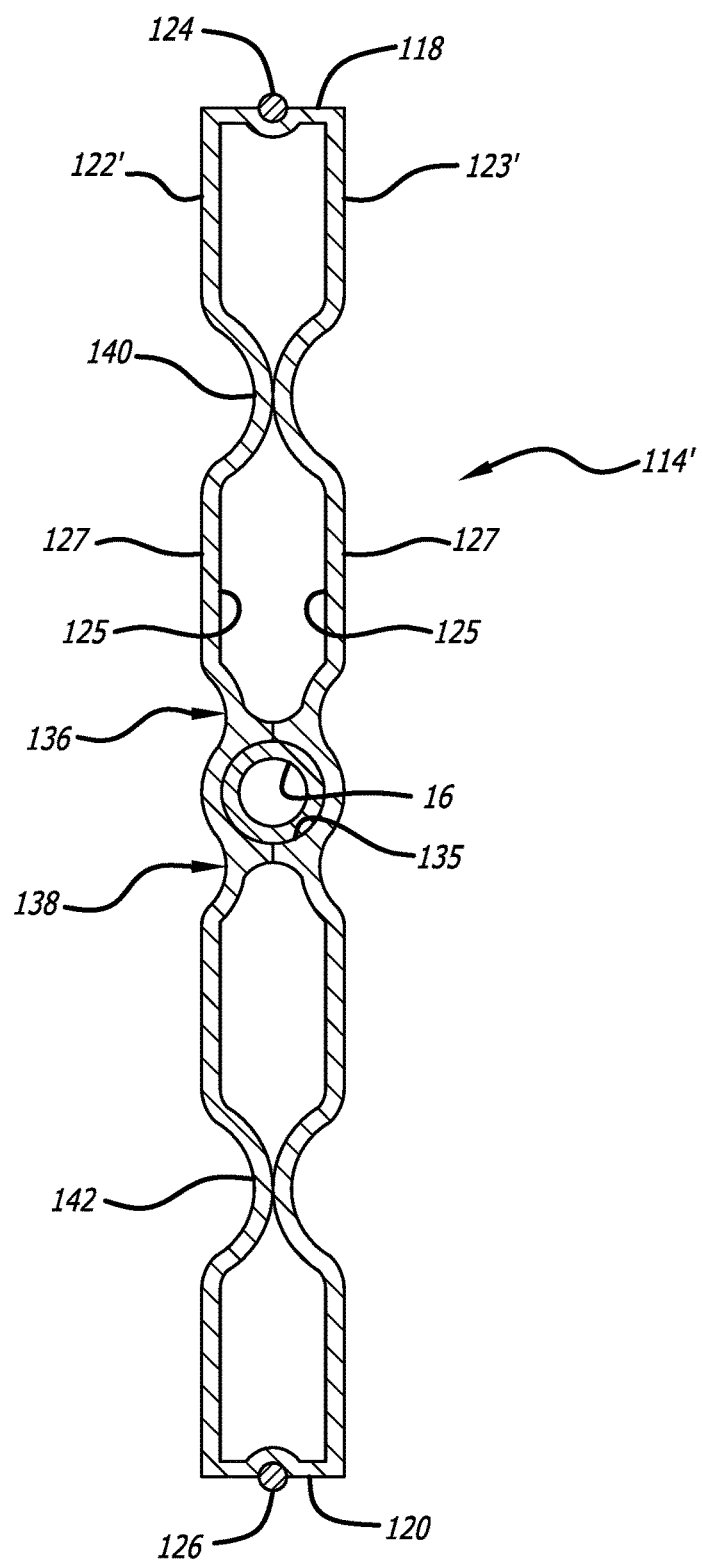
FIG. 6 is a sectional view of the structure in FIG. 5, taken substantially along the line 6-6 in FIG. 5.

In one embodiment, the balloon 114 may be shaped to present, when inflated, a "double helix" configuration, as exemplified in FIG. 4. In this configuration, the balloon presents two edges 118, 120 that each follow a non-intersecting helical path that winds around an axis A-A extending along the center of the catheter. Each edge 118, 120 has a substantially constant radius R from the central axis of the catheter, and the edges are spaced at even intervals along the axial length of the balloon, so that each point on one edge is matched by a point that is diametrically opposite on the other edge.

Extending along at least one balloon edge 118 is a first elongate electrode 124. (As used herein, the term electrode is contemplated to include one or more supply wires that feed electric power to a portion thereof that may be an element configured to generate and transmit thermal energy into the vessel.) In some embodiments a second electrode 126 extends along the other balloon edge 120. The electrodes may comprise simple strands of conductive wire such as copper, and may be attached to the edges 118, 120 using a suitable known heat resistant adhesive polymer. In some embodiments, the length of the electrodes may be encased in an insulating material, leaving only small lengths of the electrodes uncovered where heating is desired. In other embodiments, the electrodes may be embedded in the material making up the balloon, during the process of manufacture, and may be sealed in position using known thermal bonding and shaping techniques.

In yet further embodiments, the first and second electrodes may be replaced with means for emitting energy in the form of ultrasonic energy. The principles of the invention will follow the same principles of denervation with a source of energy. It is known in the art to apply energy in the form of ultrasonic energy for purposes of therapeutic value to a patient. See for example U.S. publication 2014/0163540 which is incorporated herein by reference.

The edges 118, 120 may be bonded into the balloon with sheets 122, 123 of material (FIG. 4) that form the balloon, so that inflation of the balloon will cause the edges 118, 120 to expand outwardly to the radial extremities of the balloon, thus to fit within a cylindrical profile that has a "double helix" configuration. This has the advantageous result that, when the balloon is expanded within a vessel, any first point of contact between balloon edge and vessel wall will be matched by a second point of contact diametrically opposite the first point; thus, first and second points will apply force vectors along a common diametric axis but in opposite directions. This feature has novel and beneficial results which are more fully described below. The results include the fact that expansion of the balloon will cause the balloon to position itself uniformly and centrally within the vessel, and will apply a uniform and even force that urges electrodes 124, 126 extending along edges 118, 120, against the vessel wall. At the same time, the shape of the balloon allows blood to flow through the vessel adjacent the balloon, because the shape includes continuous creases 150 in the external surface 127 of the balloon profile that define the double helix formed by the edges. This effect has the dual advantage of not blocking blood flow during treatment, as well as allowing the blood to cool the site of contact between the vessel wall and the electrodes, as is explained more fully below.

Manufacture of Balloon

In some embodiments, the balloon 114 may be given its double helical shape in the following manner. The description of the balloon under construction is accompanied by reference numerals marked with a "prime" to indicate a similar element as that shown by the same numeral in the description above, but indicates that the balloon's configuration may be different while under construction. Accordingly, a catheter is prepared to receive a deflated balloon 114' that has an initial flat shape as exemplified in FIG. 5. While a rectangular shape is desirable, other shapes are possible in which the radially extending ends of the deflated balloon may have non-linear and/or non-parallel configurations, but where the longitudinal edges 118', 120' are substantially linear and parallel to each other. The deflated balloon 114' is formed from what initially may be a cylindrical tube of suitable polymer material, but which is flattened, in a deflated state, to provide two opposing sheets 122', 123' connected to each other at the longitudinal sides by edge pieces 118' and 120'. The proximal and distal ends of the balloon may be closed off with end pieces 128 and 130. Alternatively, the proximal and distal ends may simply be directly connected to each other by a suitable adhesive, or thermal bonding. Further, two pinch lines 136 and 138 may be imparted to the balloon, in which opposite sheets 122' 123' are connected to each other on internal surfaces 125 which are internal to the balloon 114 along two linear lines to provide a small pinch space 135 (seen FIG. 6) configured to receive the catheter 16 which may be slidingly inserted into the pinch space. Pinch lines may be formed by a suitable polymer adhesive or by applying heat for thermal bonding along a line on one of the polymer sheets which is in close abutment to an adjacent sheet. The heat causes the polymer material of the sheets to bond together along a pinch line. Heat may be applied in the form of a laser beam, or may be applied by a thin conduction element configured to heat up upon the application of an electric current in known manner.

When configured as thus described, the balloon 114' is mounted on the catheter by inserting the catheter through openings 132, 134 in the distal and proximal ends of the balloon, and is slid along inside the pinch space 135 formed by the pinch lines 136, 138. The balloon 114' is positioned over a distal port of an inflation lumen (not shown, but see U.S. Pat. No. 7,951,259 incorporated herein by reference) that extends along the catheter 16 from the proximal end thereof in known manner. Only one end (preferably the distal end) of the balloon 114' is initially fixed to the catheter 16 by suitable adhesive or thermal bonding in known manner. At this stage of the balloon assembly, the electrodes 124 and 126 may be attached to the elongate edges of the balloon. Attachment may be accomplished by applying a suitable adhesive to the electrodes before compressing them onto the balloon, or by heating in combination with adhesive.

A small quantity of air may then be pumped into the balloon via the inflation lumen, in order to partially inflate the balloon and provide it with some rigidity so that it assumes the general shape of a flat rectangular balloon. In this somewhat rigid state, the proximal and distal ends of the balloon may be twisted in opposite directions, so that the balloon assumes the general double helical shape exemplified in FIG. 4. In this preliminary condition, the catheter 16 may then be bonded to the balloon 114 by applying a suitable adhesive into the pinch space 135, or by thermal bonding along the length of the catheter in contact with the balloon, so that the twisted shape of the balloon is captured and fixed in relation to the catheter when mounted onto the catheter. The balloon may then be deflated by extracting the air inside it, and the balloon sheets, along with the electrodes attached to the edges 118, 120, may be wrapped around the catheter to be ready for eventual deployment.

It can be appreciated by one of ordinary skill that bonding the balloon to the catheter along the pinch space 135 in a twisted configuration facilitates maintaining the double helical shape of the balloon edges when the balloon is inflated. For, without such bonding, the balloon might tend to untwist, and simply tend to expand outwardly at all points by an equal amount, so that the balloon might tend to assume a spherical, or near-spherical shape. However, by restraining the balloon to maintain its twisted shape through connection to the catheter 16, the balloon will tend, when inflated, to form a helix wherein the two outer edges 118, 120 form a double helix shape, (including also the electrodes affixed thereto). The edges 118, 120 thus occupy the maximum outer radius "R" of the balloon (FIG. 1). At the same time creases 150 or grooves of open space twist around the balloon in a double helix and allow a continuous passage for blood to pass along the length of the balloon when the balloon is deployed and inflated in a vessel of a patient.

In some embodiments, the balloon may be configured to more faithfully maintain a double helix shape upon inflation, while also maintaining the patency of the creases 150 of open space defined by and surrounding the balloon, for allowing the passage of blood past the balloon. In order to achieve this result, further pinch lines 140, 142 may be included in the balloon, by which opposing polymer sheets 122, 123 suitable for balloon fabrication, are bonded to each other along a plurality of lines extending parallel to the elongate axis A-A of the catheter. Additionally, yet further pinch lines 144 may be included which extend radially outward from the axis A-A of the catheter. It will be appreciated that small gaps or discontinuities must be left in all pinch lines to permit inflation medium to migrate between all the spaces in the balloon enveloped between the internal surfaces 125 of the sheets 122, 123. However, the provision of a plurality of elongate and radially extending pinch lines will compel the balloon to more faithfully adhere to a double helix shape upon expansion by pressurization, in which outer edges 118, 120 extend helically at a substantially constant radial distance away from the catheter axis A-A, and clearly defined creases 150 also extend helically around the balloon to provide a passage for blood in a vessel to flow past the balloon when the balloon is in an expanded condition. In other embodiments, opposing sheets may be bonded to each other to include a matrix of discrete points 148, that do not necessarily follow any straight lines. It can be appreciated that the more points (or lines) of connection between the opposing sheets, the closer the balloon will adhere to the desired shape defined by edges and creases, when the balloon is inflated. For example, the balloon 114 may have a compliant or semi-compliant balloon construction that tends to maintain its predesigned shape. The length of the balloon may range from about 120 mm to about 150 mm and the diameter of the balloon, when inflated, may range from about 5 mm to about 20 mm. This range of length and width of the balloon 114 may be modified to ensure that, when urged into contact with the inner renal artery wall upon inflation of the balloon, the contacting portions of the electrodes complete as least one 360 degree helical turn of the renal artery. As used herein, the term "crease" defines a depression in the balloon extending from a proximal to a distal end of the balloon, the depression being sufficient to permit blood or other body fluid to flow past the balloon while the balloon is expanded into contact with a vessel along the edges of the balloon.

As noted, in some embodiments, the one or two electrodes 124, 126 may be electrically coupled to a field generator 26 for production and delivery of electric energy to target neural fibers. In some embodiments, one or more of the electrode(s) 124, 126 may comprise Peltier electrodes for heating or cooling the target neural fibers to modulate the fibers. The electrode(s) 124, 126 may be individually assignable and may be utilized in a bipolar fashion, and/or may be utilized in a monopolar fashion with an external ground pad attached to the exterior of the patient.

Furthermore, the balloon 114 itself may be utilized as a thermal element. For example, it may be inflated with a chilled fluid that serves as a heat sink for removing heat from tissue that contacts the shaping element. Conversely, the balloon may be inflated with a warmed fluid that heats tissue in contact with the element. The thermal fluid within the shaping element optionally may be circulated and/or exchanged within the balloon 114 to facilitate more efficient conductive and/or convective heat transfer.

The apparatus 10, additionally may comprise one or more sensors, such as thermocouples (not shown) for monitoring the temperature or other parameters of the target tissue, the non-target tissue, the electrodes, the balloon and/or any other portion of the apparatus 10 or of the patient's anatomy. The treatment regime may be controlled using the measured parameter(s) as feedback. This feedback may be used, for example, to maintain the parameter(s) below a desired threshold, for example, a threshold that may cause injury to the non-target tissues. Conversely, the feedback may be used to maintain the parameter(s) at or above a desired threshold, for example, a threshold that may induce a desired effect in the target tissues, such as neuromodulation of target neural fibers or denervation of tissues innervated by the target neural fibers. Furthermore, the feedback may be used to keep the parameter(s) within a range that will induce the desired effect in the target tissues without injuring the non-target tissues to an unacceptable extent. Multiple parameters (or the same or multiple parameters at multiple locations) optionally may be used as control feedback for ensuring the desired effects while mitigating the undesired effects while mitigating the undesired effects.

Delivery and Use

The catheter 10 may be delivered to a treatment site within the artery (or within a vein or any other vessel in proximity to target neural fibers) in a low profile delivery configuration, for example, through a guide catheter or sheath.

Figure 7:
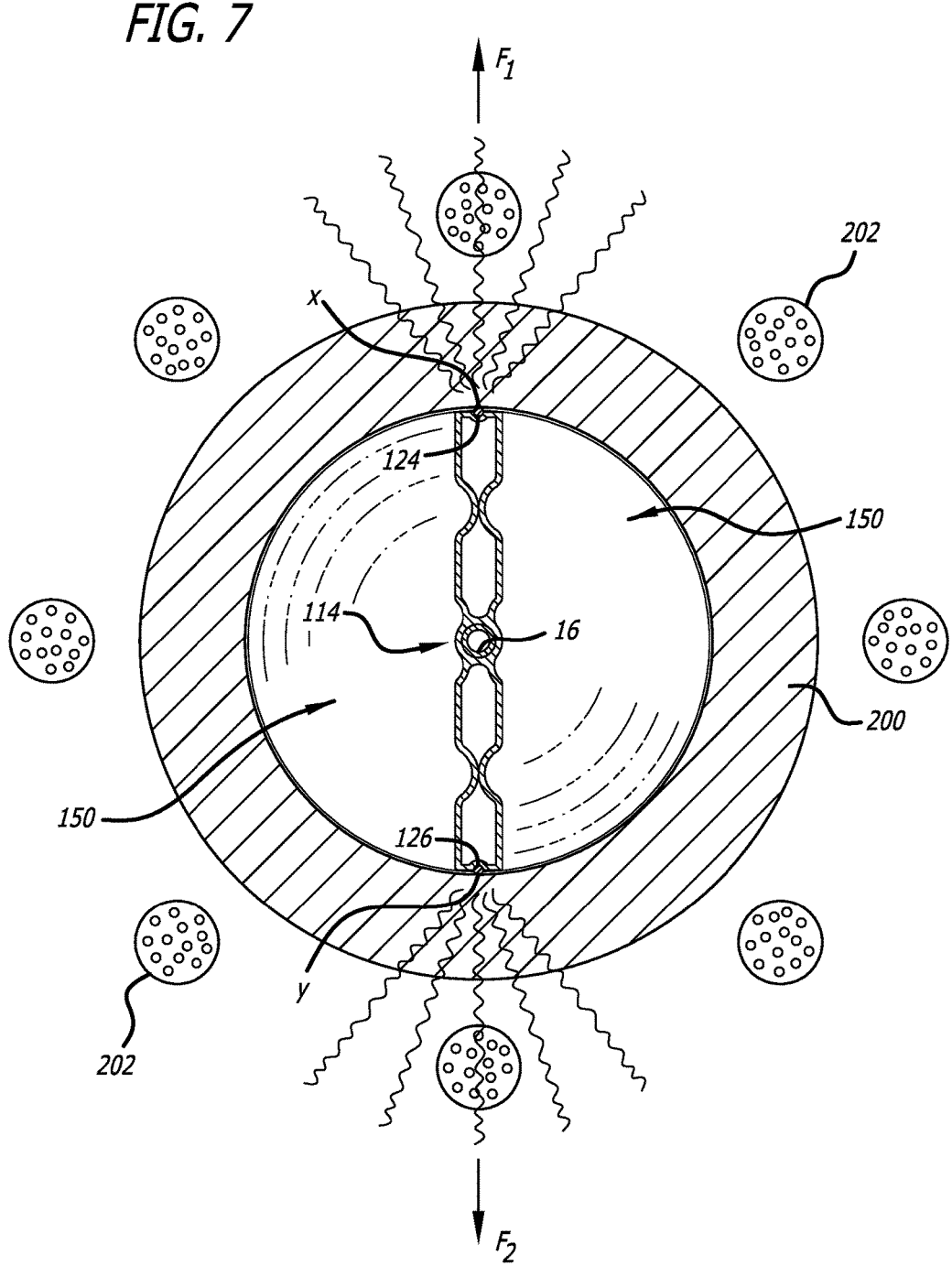
FIG. 7 is a schematic sectional view of a vessel into which the embodiment in FIG. 4 has been deployed.

With reference to FIG. 7, once positioned within the vasculature as desired, the balloon 114 may be expanded to display the electrode(s) 124, 126 and bring the electrode(s) into contact with an interior wall of the vessel 200, as seen in FIG. 7, where the electrodes apply equal but opposite forces F1 and F2 against the vessel wall. An electric current then may be generated by the field generator 26, which may be transferred through the catheter 16 to the electrode(s) 124, 126, and delivered via the electrode(s) across the wall of the artery. The electric field modulates the activity along neural fibers 202 within the wall or adventia of the artery or in proximity to the artery, e.g., at least partially denervates tissue or organ(s) innervated by the neural fibers. This may be achieved, for example, via ablation or necrosis or via non-ablative injury or other changes to the target neural fibers or supporting structures. The electric field also may induce electroporation in the neural fibers.

In addition to utilizing the patient's blood as a thermal sink, a thermal fluid may be injected, infused or otherwise delivered into the vessel itself to remove excess thermal energy and protect the non-target tissues. The thermal fluid may, for example, comprise chilled or room temperature saline (e.g., saline at a temperature lower than the temperature of the vessel wall during the therapy delivery). The thermal fluid may, for example, be injected through the catheter 16 or through a guide catheter, and may be introduced into the vessel, in the vicinity of the electrodes, via micro-pores 152 (FIG. 4) in the wall of the balloon.

Convective or other heat transfer between the non-target vessel wall tissue and the infusate may facilitate cooling (heating) of the vessel wall at a faster rate than cooling (heating) occurs at the target neural fibers. This heat transfer rate discrepancy between the wall of the vessel and the target neural fibers may be utilized to modulate the neural fibers with reduced damage to the vessel wall.

Thus, there is described a shaping structure to apply a source of energy within a body vessel which advantageously forces the energy source such as an electrode onto the wall of the vessel, while at the same time permitting blood to flow past and around the shaping structure, thereby permitting both cooling effects in the vicinity of the energy source and permitting blood to continue to supply organs of the body with oxygen.

Although preferred illustrative variations of the present invention are described above, it will be apparent to those skilled in the art that various changes and modifications may be made thereto without departing from the invention. For example, it will be appreciated that combinations of the features of different embodiments may be combined to form another embodiment. Furthermore, although in the described embodiments the apparatus and methods are for conducting in a blood vessel, it should be understood that treatment alternatively may be conducted in other body lumens. It is intended in the appended claims to cover all such changes and modifications that fall within the true spirit and scope of the invention.

We claim:

1. An apparatus for vascular denervation, comprising:
a catheter configured for delivery into a vessel of a patient;
a balloon mounted on a distal tip of the catheter, the balloon being configured to be inflatable and further configured so that, upon inflation, the balloon adopts a shape that includes a first edge and a second edge that wind around each other in a double helix, the first edge and the second edge being separated from each other by a first crease and a second crease that also wind around each other in a double helix;
wherein the balloon comprises: opposing sheets of polymer material which are attached to each other along the first edge and along the second edge, each sheet having an internal surface adapted for containing inflation medium and an external surface which is reverse to the internal surface, wherein the internal surfaces of opposing sheets are connected to each other at intermittent locations such that some portions of the internal surfaces are connected and other portions of the internal surfaces are not connected, and further wherein the external surface of each sheet defines the first crease and the second crease respectively; and
a first means for delivering energy, attached to the balloon and located to extend along the first edge.

2. The apparatus of claim 1, further including a second means for delivering energy attached to the balloon and located to extend along the second edge.

3. The apparatus of claim 1, wherein the first means for delivering energy is an electrode.

4. The apparatus of claim 1, wherein a wall of the balloon comprises a plurality of micro-pores sized to permit fluid to leak out of the balloon.

5. The apparatus of claim 1, wherein the catheter has an elongate axis and the intermittent locations extend radially outward from the elongate axis of the catheter.

6. The apparatus of claim 1, wherein the catheter has an elongate axis and the intermittent locations extend parallel to the elongate axis of the catheter.

* * * * *